United States Patent [19]

Mohrs et al.

[11] Patent Number: 4,970,215

[45] Date of Patent: Nov. 13, 1990

[54] SUBSTITUTED 4-(QUINOLIN-2-YL-METHOXY)PHENYL-ACETIC ACID DERIVATIVES AND ANTI-ALLERGIC USE THEREOF

[75] Inventors: Klaus Mohrs, Wuppertal; Siegfried Raddatz, Cologne; Elisabeth Perzborn, Wuppertal; Romanis Fruchtmann, Cologne; Christian Kohlsdorfer, Erftstadt; Reiner Müller-Peddinghaus; Pia Theisen, both of Bergisch-Gladbach, all of Fed. Rep. of Germany

[73] Assignee: Bayer Aktiengesellschaft, Leverkusen, Fed. Rep. of Germany

[21] Appl. No.: 354,536

[22] Filed: May 19, 1989

[30] Foreign Application Priority Data

May 31, 1988 [DE] Fed. Rep. of Germany ....... 3818443
Jan. 6, 1989 [DE] Fed. Rep. of Germany ....... 3900261

[51] Int. Cl.$^5$ ................. C07D 215/16; C07D 403/12; A61K 31/47
[52] U.S. Cl. .................................. 514/311; 516/174; 514/314
[58] Field of Search .......................... 546/174; 514/311

[56] References Cited

FOREIGN PATENT DOCUMENTS 0181568 5/1986 European Pat. Off. .
0206751 12/1986 European Pat. Off. .

Primary Examiner—David B. Springer
Attorney, Agent, or Firm—Sprung Horn Kramer & Woods

[57] ABSTRACT

Leucotriene synthesis inhibiting substituted 4-(quinolin-2-yl-methoxy)phenyl-acetic acid derivatives of the formula

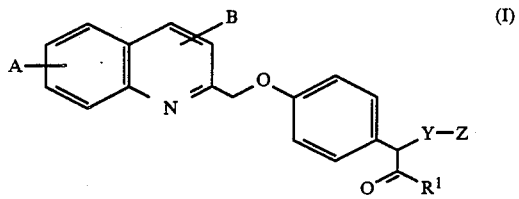

(I)

$R^1$—represents a group of the formula

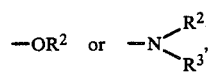

wherein
Y—represents a group of the formula

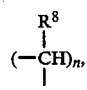

Z—represents norbornyl, or represents a group of the formula

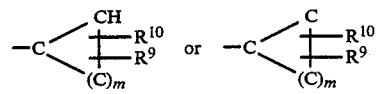

A and B are identical or different and denote hydrogen, lower alkyl or halogen, and salts thereof.

15 Claims, No Drawings

SUBSTITUTED 4-(QUINOLIN-2-YL-METHOXY)PHENYL-ACETIC ACID DERIVATIVES AND ANTI-ALLERGIC USE THEREOF

The invention relates to new substituted 4-(quinolin-2-yl-methoxy)phenylacetic acids, esters and amides thereof, processes for their preparation and their use in medicaments.

It is known that 3-(quinolin-2-yl-methoxy)phenylacetic acid and 2-[3-(quinolin-2-yl-methoxy)phenyl]propionic acid and methyl and ethyl esters thereof have an antiinflammatory and antiallergic action [compare EP-A No. 181,568].

New substituted 4-(quinolin-2-yl-methoxy)-phenylacetic acids and esters and amides thereof, of the general formula (I)

in which $R^1$—represents a group of the formula $$-OR^2 \quad \text{or} \quad -N\begin{smallmatrix}R^2\\R^3\end{smallmatrix},$$

$R^2$ and $R^3$ are identical or different and—represent hydrogen, alkyl, aryl, aralkyl or a group of the formula $$-\overset{R^4}{\underset{|}{CH}}-CO_2R^5, \quad -\overset{R^4}{\underset{|}{CH}}-CH_2-OR^5, \quad -\overset{R^4}{\underset{|}{CH}}-O-R^6$$

or $$-\overset{R^4}{\underset{|}{CH}}\underset{O\diagdown\underset{\overset{\|}{O}}{C}\diagup O}{\overset{}{\diagup}}R^7,$$

wherein $R^4$—represents hydrogen, alkyl, aralkyl or aryl, which can optionally be substituted by hydroxyl, carboxyl, alkoxycarbonyl, alkylthio, heteroaryl or carbamoyl, $R^5$—represents hydrogen, alkyl, aryl or aralkyl, $R^6$—represents a group of the formula $-COR^5$ or $-CO_2R^5$, wherein $R^5$ has the abovementioned meaning, $R^7$—represents hydrogen, alkyl or aryl, Y—represents a group of the formula $$(-\overset{R^8}{\underset{|}{CH}})_n,$$

$R^8$—represents hydrogen, alkyl or aryl and n—denotes a number from 0 to 5,

Z—represents norbornyl, or represents a group of the formula $$-C\overset{CH}{\underset{(C)_m}{\diagdown}}\overset{R^{10}}{\underset{R^9}{\diagup}} \quad \text{or} \quad -C\overset{C}{\underset{(C)_m}{\diagdown}}\overset{R^{10}}{\underset{R^9}{\diagup}}$$

wherein $R^9$ and $R^{10}$ are identical or different and denote hydrogen, alkyl or aryl, or $R^9$ and $R^{10}$ can together form a saturated carbocyclic ring having up to 6 carbon atoms and m—denotes a number from 1 to 6, and A and B are identical or different and denote hydrogen, lower alkyl or halogen, and salts thereof, have been found.

In comparison with the compounds known from EP-A 181,568, the quinolines of the general formula (I) according to the invention surprisingly have a higher in vitro activity than leucotriene synthesis inhibitors and a more potent in vivo action following oral administration.

Alkyl in general represents a straight-chain or branched hydrocarbon radical having 1 to 12 carbon atoms. Lower alkyl having 1 to about 6 carbon atoms is preferred. Examples which may be mentioned are methyl, ethyl, propyl, isopropyl, butyl, tert.-butyl, isobutyl, pentyl, isopentyl, hexyl, isohexyl, heptyl, isoheptyl, octyl and isooctyl.

Halogen in general represents fluorine, chlorine, bromine or iodine, preferably fluorine, chlorine or bromine. Halogen particularly preferably represents fluorine or chlorine.

Aryl in general represents an aromatic radical having 6 to about 12 carbon atoms. Preferred aryl radicals are phenyl, naphthyl and biphenyl.

Aralkyl in general represents an aryl radical which has 7 to 14 carbon atoms and is bonded via an alkylene chain. Aralkyl radicals having 1 to 6 carbon atoms in the aliphatic part and 6 to 12 carbon atoms in the aromatic part are preferred. The following aralkyl radicals may be mentioned as examples: benzyl, naphthylmethyl, phenethyl and phenylpropyl.

Alkylthio in general represents a straight-chain or branched hydrocarbon radical which has 1 to 12 carbon atoms and is bonded via a sulphur atom. Lower alkylthio having 1 to about 6 carbon atoms is preferred. An alkylthio radical having 1 to 4 carbon atoms is particularly preferred.

Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio and isooctylthio.

Alkoxycarbonyl can be represented, for example, by the formula $$-\underset{\overset{\|}{O}}{C}-OAlkyl$$

Alkyl in this formula represents a straight branched hydrocarbon radical having 1 to 12 carbon atoms. Lower alkoxycarbonyl having 1 to about 6 carbon atoms in the alkyl part is preferred. Alkoxycarbonyl having 1 to 4 carbon atoms in the alkyl part is particularly preferred. The following alkoxycarbonyl radicals may be mentioned as examples: methoxycarbonyl, ethoxycarbonyl, propoxycarbonyl, isopropoxycarbonyl, butoxycarbonyl and isobutoxycarbonyl.

Heteroaryl in the context of the abovementioned definition in general represents a 5- to 6-membered aromatic ring which can contain oxygen, sulphur and/or nitrogen as hetero atoms and onto which a further aromatic ring can be fused. 5- and 6-membered aromatic rings which contain an oxygen, a sulphur and/or up to 2 nitrogen atoms and which are optionally benzo-fused are preferred. Particularly preferred heteroaryl radicals which may be mentioned are: thienyl, furyl, pyridyl, pyrimidyl, pyrazinyl, pyridazinyl, quinolyl, isoquinolyl, quinazolyl, quinoxalyl, thiazolyl, benzothiazolyl, isothiazolyl, oxazolyl, benzoxazolyl, isoxazolyl, imidazolyl, benzimidazolyl, pyrazolyl, indolyl and isoindolyl.

Physiologically acceptable salts are preferred in the context of the present invention. Physiologically acceptable salts of the substituted 4-(quinolin-2-ylmethoxy)phenylacetic acids, esters and amides can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention are furthermore salts of monovalent metals, such as alkali metals and ammonium salts. Sodium, potassium and ammonium salts are preferred.

Preferred compounds of the general formula (I) are those in which

R$^1$—represents a group of the formula

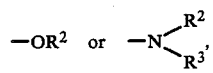

wherein

R$^2$ and R$^3$ are identical or different and—represent hydrogen, lower alkyl, benzyl, phenyl or a group of the formula

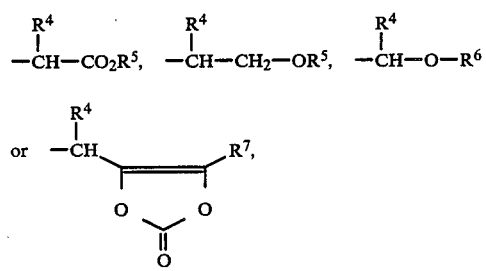

wherein

R$^4$—represents hydrogen, lower alkyl, benzyl or phenyl, which can optionally be substituted by hydroxyl, lower alkoxycarbonyl, carboxyl, lower alkylthio, heteroaryl or carbamoyl, R$^5$—represents hydrogen, lower alkyl, phenyl or benzyl, R$^6$—represents a group of the formula —COR$^5$ or —CO$_2$R$^5$, wherein R$^5$ has the above-mentioned meaning, and R$^7$—represents hydrogen, lower alkyl or phenyl, Y—represents a group of the formula

wherein

R$^8$—represents hydrogen, lower alkyl or phenyl, and n—denotes a number from 0 to 5, Z—represents norbornyl, or represents a group of the formula

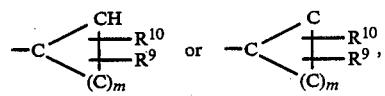

wherein

R$^9$ and R$^{10}$ are identical or different and denote hydrogen, lower alkyl or phenyl, or R$^9$ and R$^{10}$ can together form a saturated carbocyclic ring having up to 6 carbon atoms and m—denotes a number from 1 to 6, A and B are identical or different and denote hydrogen, methyl, ethyl, fluorine, chlorine or bromine, and salts thereof.

Particularly preferred compounds of the general formula (I) are those in which

R$^1$—represents a group of the formula

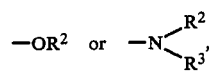

wherein

R$^2$ and R$^3$ are identical or different and—represent hydrogen, methyl, ethyl, propyl, isopropyl, butyl, tert.-butyl, phenyl or benzyl, or represent a group of the formula

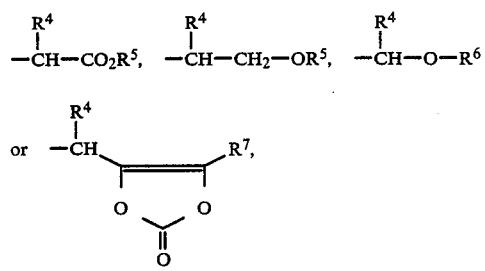

wherein

R$^4$—represents hydrogen, methyl, ethyl, propyl, isopropyl, butyl, tert.-butyl, benzyl or phenyl, which can optionally be substituted by hydroxyl, methoxycarbonyl, ethoxycarbonyl, propoxycarbonyl, carboxyl, methylthio, ethylthio, propylthio, imidazolyl or carbamoyl, R$^5$—represents hydrogen, methyl, ethyl, propyl, isopropyl, butyl, tert.-butyl, phenyl or benzyl, R[6]—represents a group of the formula —COR[5] or —CO$_2$R[5], wherein
R[5] has the abovementioned meaning,
and
R[7]—represents hydrogen, methyl, ethyl, propyl, isopropyl, butyl, tert.-butyl or phenyl,
Y—represents a group of the formula

wherein
R[8]—represents hydrogen, methyl, ethyl, propyl, isopropyl, butyl, tert.-butyl or phenyl,
and
n—denotes a number from 0 to 5,
Z—represents norbornyl or represents a group of the formula

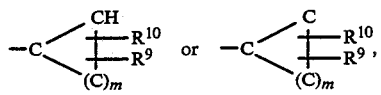

wherein
R[9] and R[10] are identical or different and denote hydrogen, methyl, ethyl, n-propyl, iso-propyl, butyl or tert.-butyl, or
R[9] and R[10] can together form a saturated carbocyclic ring having up to 6 carbon atoms and
m—denotes a number from 1 to 6, and
A and B are identical or different and denote hydrogen, methyl, ethyl, fluorine or chlorine, and salts thereof.

Especially preferred compounds of the general formula (I) are those in which
R[1]—represents a group of the formula

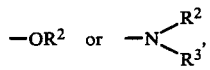

wherein
R[2] and R[3] are identical or different and—represent hydrogen or methyl, or—represent a group of the formula

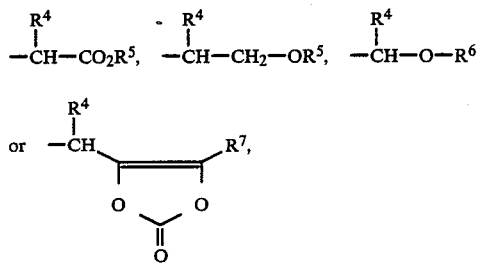

wherein
R[4]—represents hydrogen, methyl or phenyl,
R[5]—represents hydrogen, methyl, ethyl, tert.-butyl or benzyl,
R[6]—represents a group of the formula —COR[5], wherein R[5] has the abovementioned meaning, and
R[7]—represents methyl,
Y—represents a group of the formula

wherein
R[8]—represents hydrogen or methyl,
and n—denotes the number 0 or 1,
Z—represents norbornyl, or represents a group of the formula

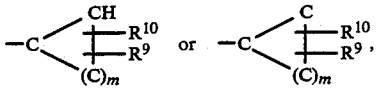

wherein
R[9] and R[10] are identical or different and denote hydrogen or methyl, or
R[9] and R[10] together form a cyclohexyl ring, and
m—denotes the number 1, 2, 3, 4 or 5, and
A and B denote hydrogen or fluorine, and salts thereof.

The compounds according to the invention can be in stereoisomeric forms which either behave as image and mirror image (enantiomers) or do not behave as image and mirror image (diastereomers). The invention relates both to the antipodes and to the racemic forms as well as the diastereomer mixtures. The racemic forms, like the diastereomers, can be resolved into the stereoisomerically uniform constituents in a known manner (compare E. L. Eliel, Stereochemistry of Carbon Compounds, McGraw Hill, 1962).

The following active compounds may be mentioned specifically:
methyl 2-[4-(quinolin-2-yl-methoxy)phenyl]-3-cyclopropylpropionate
methyl 2-[4-(quinolin-2-yl-methoxy)phenyl]-3-cyclohexylpropionate
methyl 2-[4-(quinolin-2-yl-methoxy)phenyl]-2-cyclopentylacetate
methyl 2-[4-(quinolin-2-yl-methoxy)phenyl]-2-cyclohexylacetate
methyl 2-[4-(quinolin-2-yl-methoxy)phenyl]-2-cycloheptylacetate
2-[4-(quinolin-2-yl-methoxy)phenyl]-3-cyclopropyl-propionic acid
2-[4-(quinolin-2-yl-methoxy)phenyl]-3-cyclohexyl-propionic acid
2-[4-(quinolin-2-yl-methoxy)phenyl]-2-cyclopentyl-acetic acid
2-[4-(quinolin-2-yl-methoxy)phenyl]-2-cyclohexyl-acetic acid
2-[4-(quinolin-2-yl-methoxy)phenyl]-2-cycloheptyl-acetic acid
methyl 2-[4-(quinolin-2-yl-methoxy)phenyl]-2-(cyclohex-2-enyl)-acetate
benzyloxycarbonylmethyl 2-[4-(quinolin-2-yl-methoxy)phenyl]-2-cyclopropyl-propionate
benzyloxycarbonylmethyl 2-[4-(quinolin-2-yl-methoxy)phenyl]-2-cyclopentyl-acetate 2-[4-(quinolin-2-yl-methoxy)-phenyl]-2-cyclopentylacetic acid methoxycarbonylmethylamide
methyl 2-[4-(quinolin-2-yl-methoxy)phenyl]-2-(1-decalinyl)acetate
tert.-butoxycarbonylmethyl 2-[4-(quinolin-2-yl-methoxy)phenyl]-2-cyclopentyl-acetate pivaloyloxymethyl 2-[4-(quinolin-2-yl-methoxy)-phenyl]-2-cyclopentyl-acetate
methoxycarbonylmethyl 2-[4-(quinolin-2-yl-methoxy)-phenyl]-2-cyclopentyl-acetate
2-[4-(quinolin-2-yl-methoxy)phenyl]-2-(1-decalinyl)-acetic acid
2-[4-(quinolin-2-yl-methoxy)phenyl]-2-cyclopentyl-acetic acid carboxymethylamide
sodium 2-[4-(quinolin-2-yl-methoxy)phenyl]-2-cyclopentylacetate
methyl 2-[4-(quinolin-2-yl-methoxy)phenyl]-3-cyclopentylpropionate
2-[4-(quinolin-2-yl-methoxy)phenyl]-3-cyclopentylpropionic acid
2-[4-(quinolin-2-yl-methoxy)phenyl]-2-(cyclohex-2-enyl)acetic acid
carboxymethyl 2-[4-(quinolin-2-yl-methoxy)phenyl]-2-cyclopentylacetate
methyl 2-[4-(6-fluoroquinolin-2-yl-methoxy)phenyl]-2-cyclopentylacetate
2-[4-(6-fluoroquinolin-2-yl-methoxy)phenyl-2-cyclopentylacetic acid
methyl 2-[4-(quinolin-2-yl-methoxy)phenyl]-2-norbornylacetate
2-[4-(quinolin-2-yl-methoxy)phenyl]-2-norbornyl-acetic acid
2-[4-(quinolin-2-yl-methoxy)phenyl]-2-cyclopentyl-acetic acid [(L)-2-hydroxy-1-phenylethyl]amide (both diastereomers)
(+)-4-[2-(quinolin-2-yl-methoxy)phenyl]-2-cyclopentylacetic acid and
(−)-4-[2-(quinolin-2-yl-methoxy)phenyl]-2-cyclopentylacetic acid Processes for the preparation of the compounds of the general formula (I)

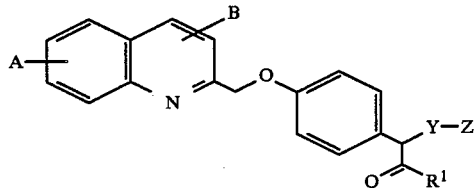
(I)

in which
A, B, $R^1$, Y and Z have the abovementioned meaning, have furthermore been found, which are characterized in that

[A] 4-(quinolin-2-yl-methoxy)phenylacetic acid esters of the general formula (Ia)

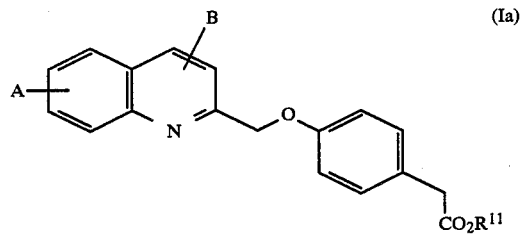
(Ia)

in which
$R^{11}$—represents alkyl and
A and B have the abovementioned meaning, are alkylated with compounds of the general formula (II)

Y—Z—X (II)

in which
Y and Z have the abovementioned meaning and
X—represents chlorine, bromine or iodine, and in the case of the acids the esters are hydrolyzed, or in that

[B] the acids of the general formula (Ib)

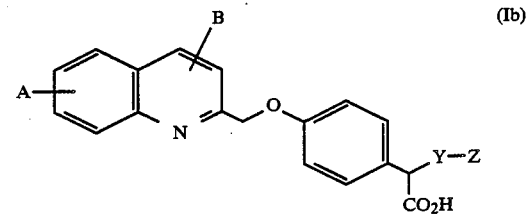
(Ib)

in which
A, B, Y and Z have the abovementioned meaning, are esterified with compounds of the general formula (III)

X—$R^{12}$ (III)

in which
$R^{12}$—represents a group of the formula

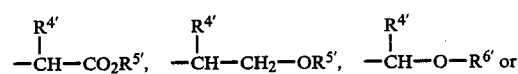

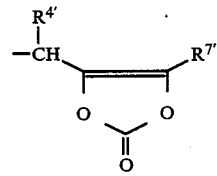

wherein
$R^{4'}$—represents alkyl, aralkyl or aryl, which can optionally be substituted by hydroxyl, carboxyl, alkoxycarbonyl, alkylthio, heteroaryl or aminocarbonyl,
$R^{5'}$—represents alkyl, aryl or aralkyl,
$R^{6'}$—represents a group of the formula —$COR^{5'}$ or —$CO_2R^{5'}$,
wherein
$R^{5'}$ has the abovementioned meaning,
$R^{7'}$—represents alkyl or aryl,
and
X has the abovementioned meaning,
and in the case of the acids the esters are subjected to hydrogenolytic cleavage, or in that

[C] the acids of the general formula (Ib) are amidated with amines of the general formula (IV)

$HN\begin{smallmatrix}R^2\\R^3\end{smallmatrix}$ (IV)

in which
$R^2$ and $R^3$ have the abovementioned meaning,
with the proviso that $R^5$ does not denote hydrogen if $R^2$ or $R^3$ represents the group

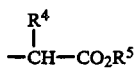

wherein
R[4] and R[5] have the abovementioned meaning,
in the presence of customary activating reagents, and in the case of the acids the esters are hydrolyzed, or in that

[D] phenols of the general formula (V)

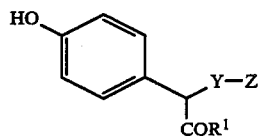
(V)

in which
R[1], Y and Z have the abovementioned meaning, are etherified with
2-halogenomethylquinolines of the formula (VI)

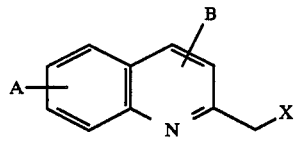
(VI)

in which
A, B and X have the abovementioned meaning, and in the case of the acids the esters are hydrolyzed.

The processes according to the invention can be illustrated by the following equations:

[A]

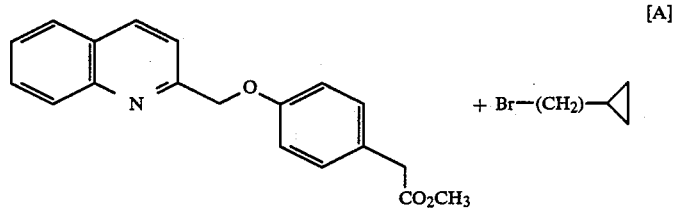

↓ Alkylation

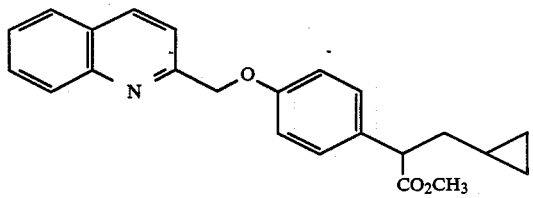

↓ Hydrolysis

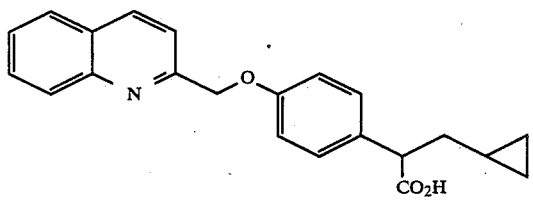

[B]

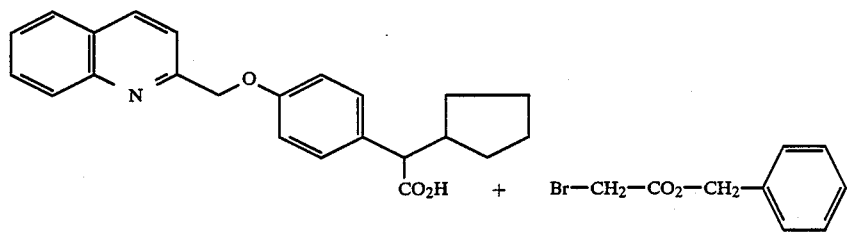

↓ Esterification

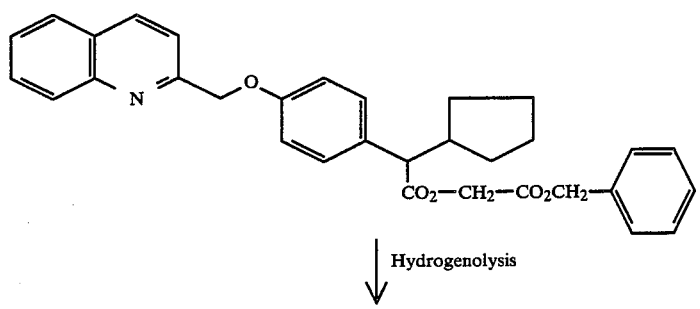
↓ Hydrogenolysis
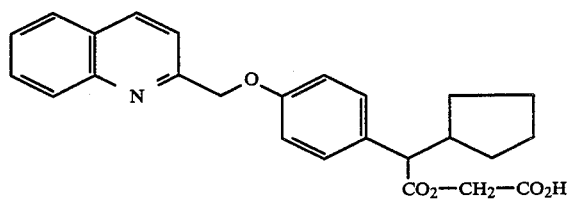
[C]
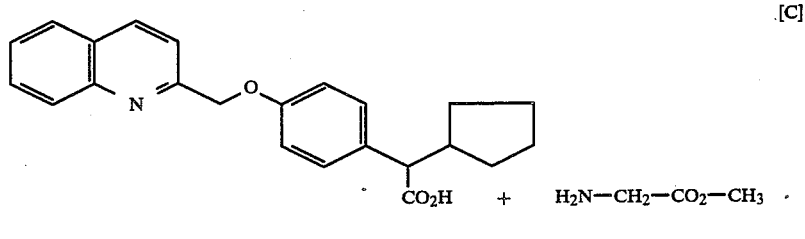
↓ Amidation
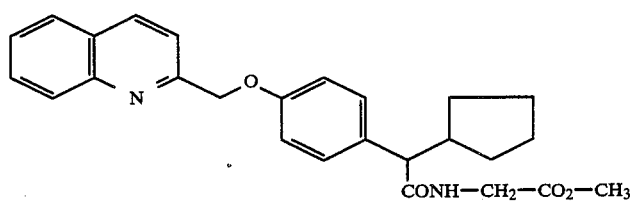
↓ Hydrolysis
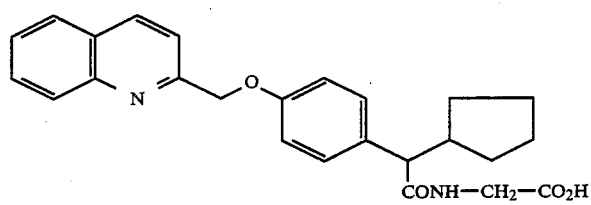
[D]
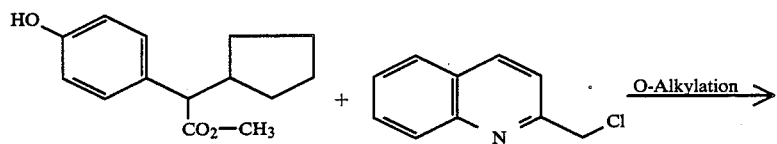

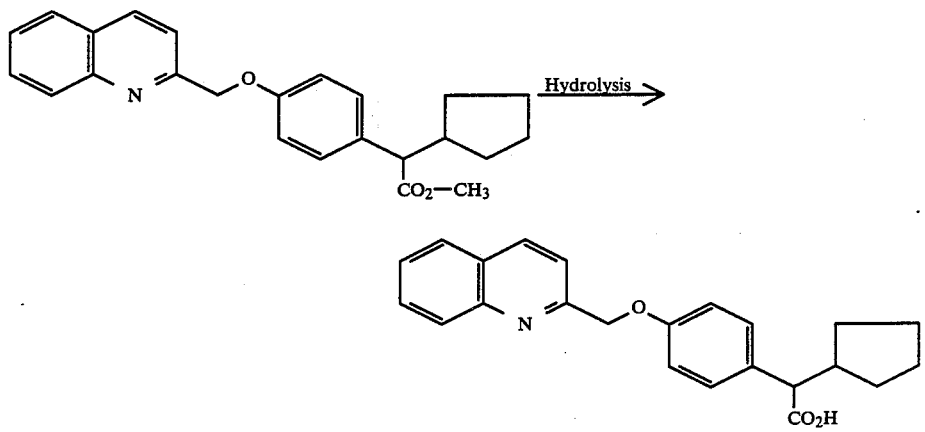

The alkylation of the C—H acid compounds (formula Ia) with alkyl halides is in general carried out in inert solvents in the presence of a base.

Suitable solvents for this reaction are all the inert organic solvents, depending on the nature of the alkylating agent. These solvents include, preferably, ethers, such as diethyl ether, dioxane or tetrahydrofuran, or hydrocarbons, such as benzene, toluene or xylene, or dimethylformamide or hexamethylphosphoric acid triamide, or mixtures of the solvents mentioned.

Suitable bases are the customary basic compounds. These include, preferably, alkali metal hydrides, such as sodium hydride, alkali metal amides, such as sodium amide or lithium diisopropylamide, alkali metal alcoholates, such as sodium methanolate, sodium ethanolate, potassium methanolate, potassium ethanolate or potassium tert.-butylate, or organic amines, such as trialkylamines, for example triethylamine, or organolithium compounds, such as butyllithium or phenyllithium.

The alkylation of the CH-acid compounds is in general carried out in a temperature range from 0° C. to 150° C., preferably from 10° C. to 100° C.

The alkylation of the CH-acid compounds is in general carried out under normal pressure. However, it is also possible to carry out the process under reduced pressure or increased pressure (for example in a range from 0.5 to 5 bar).

In general, 0.5 to 5, preferably 1 to 2, mol of halide are employed per mol of the reaction partner. The bass is in general employed in an amount of 0.5 to 5 mol, preferably 1 to 3 mole based on the halide.

The hydrolysis of the carboxylic acid esters is carried out by customary methods, by treating the esters with customary bases in inert solvents, it being possible for the salts initially formed to be converted into the free carboxylic acids by treatment with acid.

Suitable bases for the hydrolysis are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium or potassium carbonate or sodium bicarbonate, or alkali metal alcoholates, such as sodium ethanolate, sodium methanolate, potassium ethanolate, potassium methanolate or potassium tert.-butanolate. Sodium hydroxide or potassium hydroxide are particularly preferably employed.

Suitable solvents for the hydrolysis are water or the organic solvents customary for hydrolysis. These include, preferably, alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is likewise possible to employ mixtures of the solvents mentioned.

The hydrolysis is in general carried out in a temperature range from 0° C. to +100° C., preferably from +20° C. to +80° C.

The hydrolysis is in general carried out under normal pressure. However, it is also possible to carry out the hydrolysis under reduced pressure or under increased pressure (for example from 0.5 to 5 bar).

In carrying out the hydrolysis, the base is in general employed in an amount of 1 to 3 mol, preferably 1 to 1.5 mol, per mol of the ester or lactone. Molar amounts of the reactants are particularly preferably used.

In carrying out the hydrolysis, the salts of the compounds according to the invention are formed in the first step as intermediate products which can be isolated. The acids according to the invention are obtained by treatment of the salts with customary inorganic acids. These include, preferably, mineral acids, such as, for example, hydrochloric acid, hydrobromic acid, sulphuric acid or phosphoric acid. In the preparation of the carboxylic acids, it has proved advantageous here for the basic reaction mixture of the hydrolysis to be acidified in a second step without the salts being isolated. The acids can then be isolated in the customary manner.

The esterification of the carboxylic acids is carried out by customary methods by treating the acids with alkyl halides in inert solvents, if appropriate in the presence of a base.

Suitable bases are the customary organic amines. These include, preferably, alkylamines, such as triethylamine, diisopropylamine, dicyclohexylamine and ethyldiisopropylamine.

Suitable solvents here are all the inert organic solvents. These include, preferably, ethers, such as diethyl ether, dioxane or tetrahydrofuran, or hydrocarbons, such as benzene, toluene or xylene, or dimethylformamide or mixtures of the solvents mentioned.

The esterification of the carboxylic acids is in general carried out in a temperature range from 0° to 150° C., preferably from 10° C. to 100° C.

The esterification of the carboxylic acids is in general carried out under normal pressure. However, it is also possible to carry out the process under reduced pressure or increased pressure (for example in a range from 0.5 to 5 bar).

In general, 0.5 to 5, preferably 1 to 2, mol of halide per mol of the reaction partner are employed. The base is in general employed in an amount of 0.5 to 5 mol, preferably 1 to 3 mol, based on the halide.

In general, 0.01 to 1, preferably 0.05 to 0.5, mol of catalyst per mol of reaction partner is employed.

The hydrogenolytic cleavage of the benzyl esters is carried out by customary methods by hydrogenating the benzyl esters with hydrogen gas in an inert solvent in the presence of a catalyst.

Suitable catalysts are the customary metal catalysts, which are applied, if appropriate, to an inert carrier, such as, for example, charcoal, in variable concentrations. These catalysts preferably include palladium, nickel and platinum, particularly preferably 5 to 15% strength palladium-on-active charcoal.

Suitable solvents here are all the inert organic solvents. These include, preferably, ethers, such as diethyl ether, dioxane or tetrahydrofuran, or hydrocarbons, such as benzene, toluene or xylene, or alcohols, such as methanol, ethanol or propanol, or low-boiling esters, such as ethyl acetate, or amines, such as triethylamine, or mixtures of the solvents mentioned.

The hydrogenolytic cleavage is in general carried out in a temperature range from 0° C. to 150° C., preferably from 10° C. to 100° C.

The hydrogenolytic cleavage is in general carried out with hydrogen under normal pressure. However, it is also possible to carry out the process under increased pressure (for example in a range from 1 to 10 bar).

In general, 0.01 to 1, preferably 0.05 to 0.5, mol of catalyst per mol of reaction partner is employed.

The amidation of the compounds (Ib) with amines is in general carried out in inert solvents in the presence of a base.

Suitable solvents here are all the inert organic solvents, depending on the nature of the amine. These include, preferably, ethers, such as diethyl ether, dioxane or tetrahydrofuran, hydrocarbons, such as benzene, toluene or xylene, or dimethylformamide or mixtures of the solvents mentioned. Dimethylformamide is particularly preferred.

Suitable bases are the customary basic compounds. These include, preferably, organic amines, such as trialkylamines, for example triethylamine.

Suitable amine components are, in addition to the customary amines, such as, for example, propylamine, dimethylamine or diethylamine, also optically active amino acid esters, such as, for example, the esters of alanine, leucine, methionine, threonine, tyrosine, cystine, glycine, isoleucine, lysine, phenylalanine, phenylglycine or valine, or amino-alcohols, such as, for example, 2-aminoethanol or phenylglycinol/alamine, it being possible for the latter to be prepared in optically pure form by reduction of the corresponding amino acid by a known method (compare G. C. Barrett, Chemistry and Biochemistry of the Amino Acids, Chapman and Hall, 1985).

The diastereomeric amides of the compounds of the formula (I) can thus be prepared by a process analogous to process [C] described above by using the abovementioned amine components. After resolution of the diastereomers by the customary methods listed above and subsequent hydrolysis, the pure enantiomers of the compounds of the formula (I) according to the invention are obtained.

Activating reagents which are used are in general the customary peptide-coupling reagents. These include, preferably, carbodiimides, such as, for example, diisopropylcarbodiimide, dicyclohexylcarbodiimide or N-(3-dimethyl-aminoisopropyl)-N'-ethylcarbodiimide hydrochloride, or carbonyl compounds, such as carbonyldiimidazole or 1,2oxazolium compounds, such as 2-ethyl-5-phenyl-1,2-oxazolium-3-sulphonate, or propanephosphonic anhydride or isobutyl chloroformate or benzotriazolyloxy-tris-(dimethylamino)phosphonium hexafluorophosphate or phosphoric acid diphenyl esteramide or methanesulphonyl chloride, if appropriate in the presence of bases, such as triethylamine or N-ethylmorpholine or N-methylpiperidine or dicyclohexylcarbodiimide and N-hydroxysuccinimide.

The hydrolysis is in general carried out with inorganic or organic acids, such as hydrochloric acid, hydrobromic acid, sulphuric acid, phosphoric acid, formic acid, acetic acid, propionic acid, methanesulphonic acid or trifluoroacetic acid, or mixtures of the acids mentioned.

The amidation of the compounds of the general formula (I) according to the invention is in general carried out in a temperature range from 0° C. to +150° C., preferably from 0° C. to +50° C.

The amidation is in general carried out under normal pressure. However, it is also possible to carry out the process under reduced pressure or under increased pressure (for example in a range from 0.5 to 5 bar).

The esters of the general formula (Ia) used as starting compounds are also prepared from the known 4-hydroxyphenylacetic acids by etherification with 2-halogenomethylquinolines of the general formula (VI) analogously to process D.

The etherification can be carried out in inert organic solvents, if appropriate in the presence of a base.

Solvents for the etherification can be inert organic solvents which do not change under the reaction conditions. These include, preferably, ethers, such as, for example, dioxane, tetrahydrofuran or diethyl ether, halogenohydrocarbons, such as methylene chloride, chloroform, carbon tetrachloride, 1,2-dichloroethane or trichloroethylene, hydrocarbons, such as benzene, xylene, toluene, hexane, cyclohexane or petroleum fractions, nitromethane, dimethylformamide, acetonitrile, acetone or hexamethylphosphoric acid triamide. It is also possible to employ mixtures of the solvents.

Inorganic or organic bases can be employed as bases for the etherification. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or organic amines (trialkyl($C_1$–$C_6$)amines), such as triethylamine, or heterocyclic compounds, such as pyridine, methylpiperidine, piperidine or morpholine.

It is also possible for alkali metals, such as sodium, and hydrides thereof, such as sodium hydride, to be employed as bases.

The etherification to prepare compounds of the formula (Ia) is in general carried out in a temperature range from 0° C. to 150° C., preferably from 10° C. to 100° C., and in general under normal pressure. However, it is also possible to carry out the process under reduced pressure or increased pressure (for example in a range from 0.5 to 5 bar).

In general, 0.5 to 5, preferably 1 to 2, mol of halide per mol of reaction partner is employed. The base is in general employed in an amount of 0.5 to 5 mol, preferably 1 to 3 mol, based on the halide.

4-Hydroxyphenylacetic acid esters are known or can be prepared by customary methods from the corresponding phenols, suitable protective groups being split off [compare H. Beyer, Lehrbuch der organischen Chemie (Textbook of Organic Chemistry), S. Hirzel Verlag, Stuttgart; Protective Groups in Organic Synthesis, J. Wiley & Sons, 1981, New York].

The substituted 4-hydroxyphenylacetic acid esters of the general formula (V) are in most cases new and can be prepared from the abovementioned 4-hydroxyphenylacetic acid esters by alkylation by known methods (compare Ferri, Reaktionen der organischen Synthese, Georg Thieme Verlag, Stuttgart, 1978).

2-Halogenomethylquinolines of the formula (VI), such as, for example, 2-chloromethylquinoline, are known and can be prepared by customary methods [compare Chem. Berichte. 120, 649, 1987].

The compounds of the formula (II) and (III) are known or can be prepared by customary halogenation methods [compare Organikum VEB Deutscher Verlag der Wissenschaften, Berlin 1977].

The acids, esters and amides according to the invention can be employed as active compounds in medicaments. The substances have an action in particular as inhibitors of enzymatic reactions in the context of arachidonic acid metabolism, in particular of 5-lipoxygenase.

The compounds according to the invention exhibit a good action following oral administration in lipoxygenase-sensitive test models.

They are therefore preferably suitable for treatment and prevention of diseases of the respiratory tract, such as allergies/asthma, bronchitis, emphysemas, shock lung, pulmonary hypertension, inflammations/rheumatism and oedemas, thromboses and thromboembolisms, ischaemias (peripheral, cardiac and cerebral circulation disturbances), cardiac and cerebral infarctions, disturbances in cardiac rhythm, angina pectoris and arteriosclerosis, for tissue transplants, dermatoses, such as psoriasis, and metastases and for cytoprotection in the gastrointestinal tract.

The new active compounds can be converted into the customary formulations, such as tablets, capsules, coated tablets, pills, granules, aerosols, syrups, emulsions, suspensions and solutions, in a manner which is known per se using inert non-toxic pharmaceutically suitable excipients or solvents. The therapeutically active compound should in each case be present in the total mixture, here in a concentration of about 0.5 to 90% by weight, preferably 10 to 70% by weight, that is to say in amounts which suffice to achieve the stated dosage range.

The formulations are prepared, for example, by extending the active compounds with solvents and/or excipients, if appropriate using emulsifying agents and/or dispersing agents, and, for example, in the case where water is used as a diluent, organic solvents can be used, if appropriate, as auxiliary solvents.

Examples of auxiliaries which may be mentioned are: water, non-toxic organic solvents, such as paraffins (for example petroleum fractions), vegetable oils (for example groundnut/sesame oil), alcohols (for example ethyl alcohol and glycerol) and glycols (for example propylene glycol and polyethylene glycol), solid excipients, such as natural rock powders (for example kaolins, aluminas, talc and chalk), synthetic rock powders (for example highly disperse silicic acid and silicates), sugars (for example sucrose, lactose and glucose), emulsifying agents (for example polyoxyethylene fatty acid esters, polyoxyethylene fatty alcohol ethers, alkylsulphonates and arylsulphonates), dispersing agents (for example lignin-sulphite waste liquors, methylcellulose, starch and polyvinylpyrrolidone) and lubricants (for example magnesium stearate, talc, stearic acid and sodium lauryl-sulphate.

Administration can be effected in the customary manner, preferably orally or parenterally, in particular perlingually or intravenously. In the case of oral use, tablets can of course also contain, in addition to the excipients mentioned, additives such as sodium citrate, calcium carbonate and dicalcium phosphate, together with various additional substances, such as starch, preferably potato starch, gelatine and the like. Lubricants, such as magnesium stearate, sodium lauryl-sulphate and talc, can moreover be co-used for tablet-making. In the case of aqueous suspensions and/or elixirs intended for oral use, various agents for improving the taste or dyestuffs can be added to the active compounds in addition to the abovementioned auxiliaries.

In the case of parenteral use, solutions of the active compounds can be used, employing suitable liquid excipients.

In general, it has proved advantageous in the case of intravenous administration to administer amounts of about 0.01 to 10 mg/kg, preferably 0.01 to 5 mg/kg of body weight to achieve effective results. In the case of oral administration, the dosage is in general about 0.1 to 200 mg/kg, preferably 1 to 100 mg/kg of body weight.

Nevertheless, it may at times be necessary to deviate from the amounts mentioned, and in particular to do so as a function of the body weight or nature of the administration route, the individual behaviour towards the medicament, the nature of its formulation and the time or interval at which administration takes place. Thus it can in some cases suffice to manage with less than the abovementioned minimum amount, whereas in other cases the upper limit mentioned must be exceeded. Where relatively large amounts are administered, it may be advisable to divide these into several individual doses over the course of the day.

The acids and esters according to the invention can be used both in human medicine and in veterinary medicine.

Preparation Examples

EXAMPLE 1 (starting compound)

Methyl 4-(quinolin-2-yl-methoxy)phenylacetate

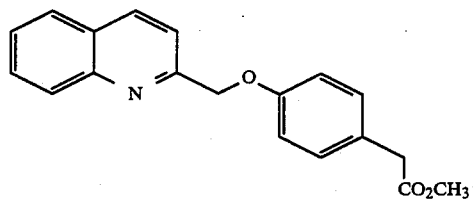

200 g (1.2 mol) of methyl 4-hydroxyphenylacetate and 166 g (1.2 mol) of potassium carbonate are stirred in 2 l of dimethylformamide at 25° C. for 1 hour. After addition of 214 g (1.2 mol) of 2-chloromethylquinoline, the mixture is heated to 50° C. for 15 hours. After concentration in vacuo, the residue is partitioned between water and ethyl acetate and the organic phase is dried over sodium sulphate and concentrated. The product which remains is recrystallized from methanol.

Yield: 293 g (79% of theory)
Melting point: 71°–73° C.

EXAMPLE 2

Methyl 2-[4-(quionlin 2-yl-methoxy)phenyl]-3-cyclopropylpropionate

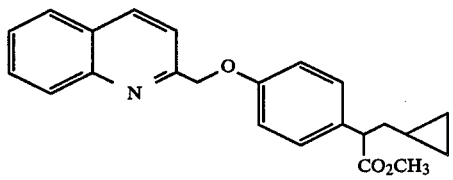

15.4 g (50 mmol) of methyl 4-(quinolin-2-yl-methoxy)-phenylacetate are added dropwise to a suspension of 1.5 g (55 mmol) of sodium hydride in 60 ml of dimethylformamide at 0° C. under an inert gas. When the evolution of hydrogen has ended, the mixture is subsequently stirred at 25° C. for 1 hour, 7.4 g (55 mmol) of (bromomethyl)-cyclopropane in 60 ml of dimethylformamide are added dropwise, while cooling with ice, and the mixture is stirred at 25° C. for 16 hours. After the solvent has been evaporated off in vacuo, the residue is partitioned between ethyl acetate and water and the organic phase is dried over sodium sulphate and concentrated. The residue is recrystallized from methanol.

Yield: 15 g (83% of theory).
Melting point: 47° C.

EXAMPLE 3

Methyl 2-[4-(quinolin-2-yl-methoxy)phenyl]-3-cyclohexylpropionate

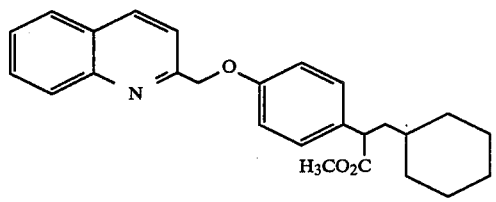

The preparation is carried out from 15.4 g (50 mmol) of methyl 4-(quinolin-2-yl-methoxy)phenylacetate and 9.74 g (55 mmol) of (bromomethyl)-cyclohexane analogously to the instructions of Example 2.

Yield: 15.9 g (79% of theory).
Melting point: 69° C.

EXAMPLE 4

Methyl 2-[4-(quinol in-2-yl-methoxy)phenyl[-2-cyclopentylacetate

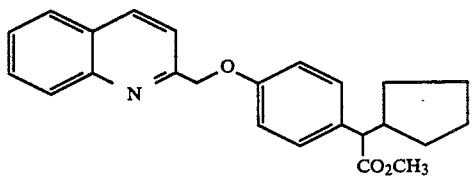

Process (a)
The preparation is carried out from 15.4 g (50 mmol) of methyl 4-(quinolin-2-yl-methoxy)phenylacetate and 8.2 g (55 mmol) of cyclopentyl bromide analogously to the instructions of Example 2.

Yield: 12.8 g (68% of theory).
Melting point: 94° C.

Process (b)
2.3 g (10 mmol) of methyl 2-(cyclopentyl-2(4-hydroxyphenyl)acetate are dissolved in 30 ml of dimethylformamide. After addition of 1.4 g (10 mmol) of potassium carbonate, the mixture is stirred at 60° C. for 1 hour, a solution of 2.3 g (10 mmol) of 2-chloromethylquinoline in 20 ml of dimethylformamide is added and the mixture is stirred at 60° C. for 15 hours. After cooling, the mixture is concentrated, the residue is taken up in ethyl acetate and the mixture is washed twice with water. After drying over sodium sulphate, the mixture is concentrated and the residue is recrystallized from methanol.

Yield: 3.18 g (85% of theory.

EXAMPLE 5

Methyl 2-[4-(quinolin-2-yl-methoxy)phenyl]-2-cyclohexylacetate

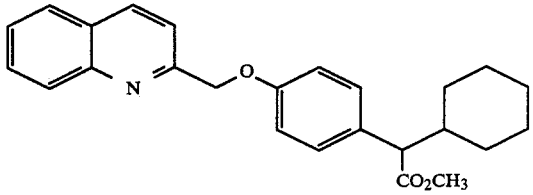

The preparation is carried out from 15.4 g (50 mmol) of methyl 4-(quinolin-2-yl-methoxy)phenylacetate and 11.55 g (55 mmol) of cyclohexyl iodide analogously to the instructions of Example 2.

Yield: 11.74 g (60% of theory).
Melting point: 92° C.

EXAMPLE 6

Methyl 2-[4-(quinolin-2-yl-methoxy)phenyl]-2-cycloheptylacetate

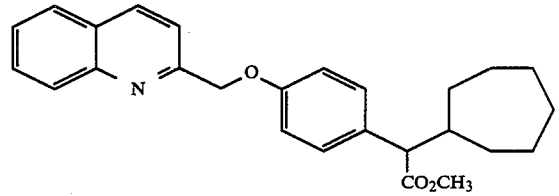

The preparation is carried out from 15.4 g (50 mmol) of methyl 4-(quinolin-2-yl-methoxy)phenylacetate and 9.07 g (55 mmol) of cycloheptyl bromide analogously to the instructions of Example 2.

Yield: 16 g (80% of theory).
Melting point: 81° C.

EXAMPLE 7

2-[4-(Quinolin-2-yl-methoxy)phenyl]-3-cyclopropyl-propionic acid

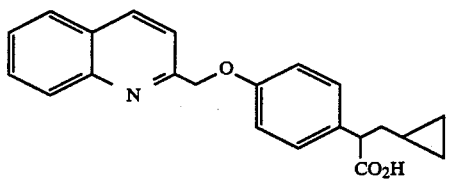

13.33 g (37 mmol) of methyl 2-[4-(quinolin-2-yl-methoxy)phenyl]-3-cyclopropyl-propionate are heated under reflux in 200 ml of methanol and 55.4 ml of 1 molar sodium hydroxide solution for 10 hours. After cooling, the mixture is acidified with concentrated hydrochloric acid and the product which has precipitated is filtered off with suction and dried.

Yield: 12.5 g (98% of theory.
Melting point: 146° C.

EXAMPLE 8

2-[4-(Quinolin-2-yl-methoxy)phenyl]-3-cyclohexyl-propionic acid

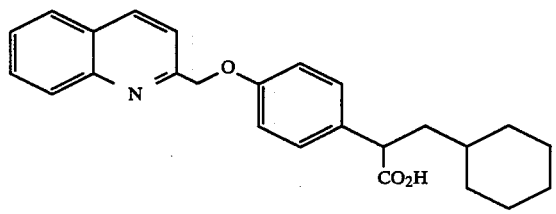

The preparation is carried out from 6.25 g (15.5 mmol) of methyl 2-[4-(quinolin-2-yl-methoxy)phenyl]-3-cyclohexylpropionate analogously to the instructions of Example 7.

Yield: 5 g (83% of theory).
Melting point: 148°-151° C.

EXAMPLE 9

2-[4-(Quinolin-2-yl-methoxy)phenyl]-2-cyclopentyla-cetic acid

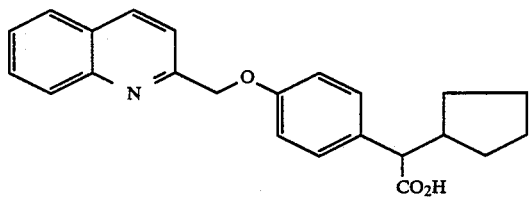

The preparation is carried out from 10.87 g (29 mmol) of methyl 2-[4-(quinolin-2-yl-methoxy)phenyl]-2-cyclopentylacetate analogously to the instructions of Example 7.

Yield: 8.8 g (84% of theory).
Melting point: 183°-185° C.

EXAMPLE 10

2-[4-(Quinolin-2-yl-methoxy)phenyl]-2-cyclohexyla-cetic acid

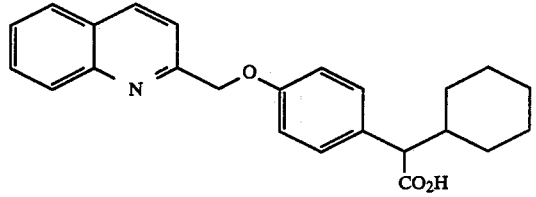

The preparation is carried out from 10 g (26 mmol) of methyl 2-[4-(quinolin-2-yl-methoxy)phenyl]-2-cyclohexylacetate analogously to the instructions of Example 7.

Yield: 8.7 g (90% of theory).
Melting point: 201°-207° C.

EXAMPLE 11

2-[4-Quinolin-2-yl-methoxy)phenyl]-2-cycloheptyla-cetic acid

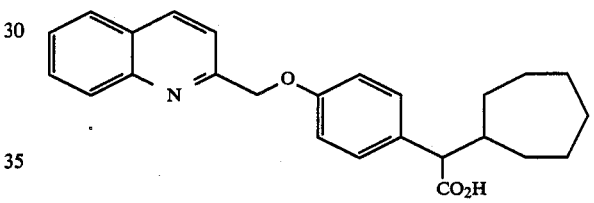

The preparation is carried out from 11 g (27 mmol) of methyl 2-[4-(quinolin-2-yl-methoxy)phenyl]-2-cycloheptylacetate analogously to the instructions of Example 7.

Yield: 9.3 g (87% of theory).
Melting point: 176° C.

EXAMPLE 12

Methyl 2-[4-(quinolin-2-yl-methoxy)phenyl]-2-(cyclohex-2enyl)acetate

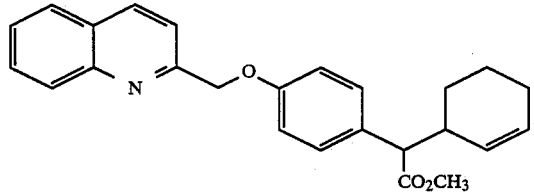

The preparation is carried out from 15.4 g (50 mmol) of methyl 4-(quinolin-2-yl-methoxy)phenylacetate and 8.86 g (55 mmol) of 3-bromocyclohexene analogously to the instructions of Example 2.

Yield: 14.74 g (76% of theory).
Melting point: 102°-104° C.

EXAMPLE 13

Benzyloxycarbonylmethyl 2-[4-(quinolin-2-yl-methoxy)phenyl]-3-cyclopropylpropionate

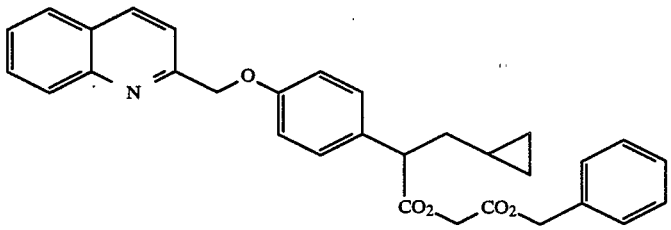

7 g of 2-[4-(quinolin-2-yl-methoxy)phenyl]-3-cyclopropylpropionic acid, 5 g of benzyl bromoacetate and 4 g of dicyclohexylamine are heated under reflux in 100 ml of tetrahydrofuran for 15 hours. After cooling to 0° C., the salt which has precipitated is filtered off and the solvent is evaporated off in vacuo. The residue is chromatographed on silica gel using methylene chloride. An oil is obtained.

Yield: 9.27 g (93% of theory).

$R_f$(HPLC)=4.30 minutes (RP 8, 7 μm; acetonitrile/water 70:30)).

EXAMPLE 14

Benzyloxycarbonylmethyl 2-[4-(quinolin-2-yl-methoxy)phenyl]-2-cyclopentylacetate

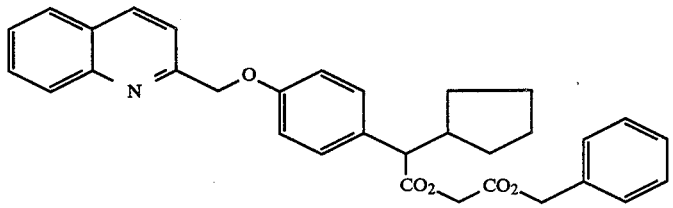

The preparation is carried out from 7.22 g (20 mmol) of 2-[4-(quinolin-2-yl-methoxy)phenyl]-2-cyclopentylacetic acid and 5 g (22 mmol) of benzyl bromoacetate analogously to the instructions of Example 13.

Yield: 8.03 g (79% of theory.

Melting point: 63°-65° C. (hydrochloride).

EXAMPLE 15

2-[4-(Quinolin-2-yl-methoxy)phenyl]-2-cyclopentylacetic acid methyloxycarbonylmethylamide

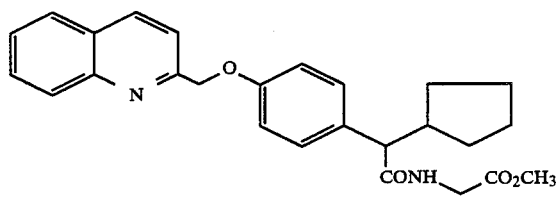

7.22 g (20 mmol) of 2-[4-(quinolin-2-yl-methoxy)-phenyl]-2-cyclopentylacetic acid and 3.0 g (24 mmol) of glycine methyl ester hydrochloride are dissolved in 75 ml of dimethylformamide. After cooling to 0° C., 6.6 g (24 mmol) of phosphoric acid diphenyl ester-azide, dissolved in 25 ml of dimethylformamide, are added dropwise and the mixture is subsequently stirred for 30 minutes. 7.3 g (72 mmol) of triethylamine are then added dropwise and the mixture is subsequently stirred at 0° C. for 4 hours and at 25° C. for 15 hours. The reaction solution is poured onto 300 g of ice and extracted three times with ethyl acetate. The organic phases are washed once with 1 normal hydrochloric acid and once with water, dried over sodium sulphate and concentrated. The product is recrystallized from methanol.

Yield: 5.34 g (62% of theory).

Melting point: 134°-136° C.

EXAMPLE 16

Methyl 2-[4-(quinolin-2-yl-methoxy)phenyl]-2-(1-decalinyl)acetate

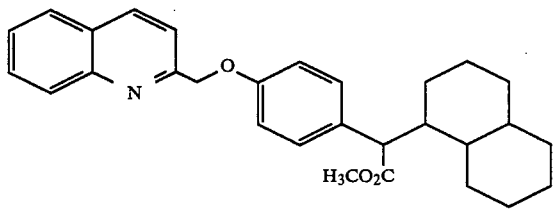

The preparation is carried out from 15.4 g (50 mmol) of methyl 4-(quinolin-2-yl-methoxy)phenyl-acetate and 9.55 g (55 mmol) of 1-chloro-decalin analogously to the instructions of Example 2.

Yield: 3.11 g (14% of theory).

Melting point: 118° C.

EXAMPLE 17 tert.-Butyloxycarbonylmethyl 2-[4-(quinolin-2-yl-methoxy)phenyl]-2-cyclopentylacetate

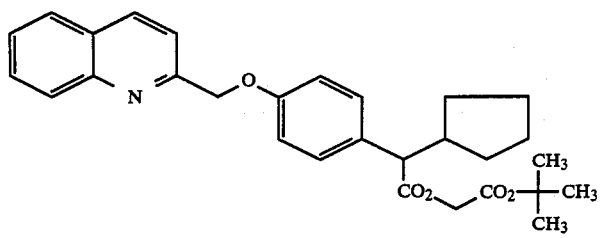

The preparation is carried out from 3 g (8.3 mmol) of 2-[4-(quinolin-2-yl-methoxy)-phenyl]-2-cyclopentyl-acetic acid and 1.77 g (9.1 mmol) of tert.-butylbromoacetate analogously to the instructions of Example 13.
Yield: 3.18 g (80.5% of theory).
Melting point: 88°–91° C.

EXAMPLE 18

Pivaloyloxymethyl 2-[4-(quinolin-2-yl-methoxy)-phenyl]-2-cyclopentylacetate

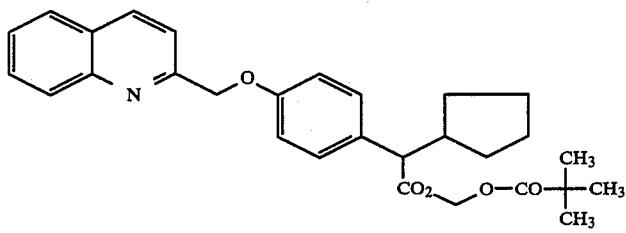

The preparation is carried out from 3 g (8.3 mmol) of 2-[4-(quinolin-2-yl-methoxy)-phenyl]-2-cyclopentyl-acetic acid an 1.37 g (9.1 mmol) of a chloromethyl pivalate analgously to the instructions of Example 13.
Yield: 1.38 g (35% of theory).
Melting point: 30°–32° C.

EXAMPLE 19

Methoxycarbonylmethyl 2-[4-(quinolin-2-yl-methoxy)phenyl]-2-cyclopenyl-acetate

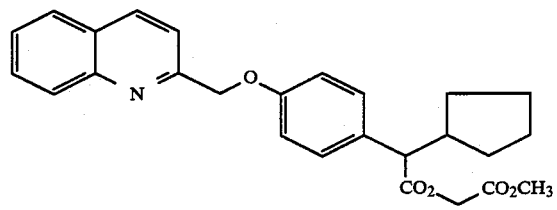

The preparation from 3 g (8.3 mmol) of 2-[4-(quinolin-2-yl-methoxy)phenyl]-2-cyclopentyl-acetic acid and 1.39 g (9.1 mmol) of methyl bromoacetate analogously to the instructions of Example 13.
Yield: 3.37 g (94% of theory).
Melting point: 90°–93° C.

EXAMPLE 20

2-[4-(Quinolin-2-yl-methoxy)phenyl]-2-(1-decalinyl)-acetic acid

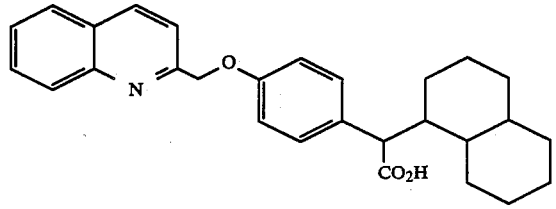

The preparation is carried out from 610 mg (1.37 mmol) of methyl 2-[4-(quinolin-2-yl-methoxy)phenyl]-2-(1-decalinyl)-acetate analogously to the instructions of Example 7.
Yield: 470 mg (80% of theory).
Melting point: 200°–207° C.

EXAMPLE 21

2-[4-(Quinolin-2-yl-methoxy)phenyl]-2-cyclopentylacetic acid carboxymethylamide

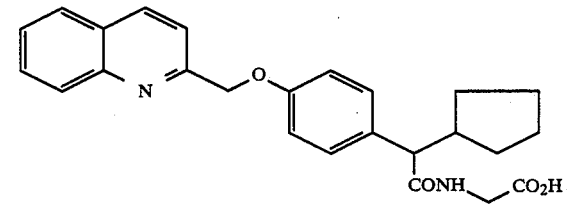

The preparation is carried out from 3 g (69 mmol) of 2-[4-(quinolin-2-yl-methoxy)-phenyl]-2-cyclopentyl-acetic acid methoxycarbonyl-methylamide analogously to the instructions of Example 7.
Yield: 2.47 g (85% of theory).
Melting point: 182°–185° C.

EXAMPLE 22

Sodium 2-[4-(quinolin-2-yl-methoxy)phenyl]-2-cyclopentylacetate

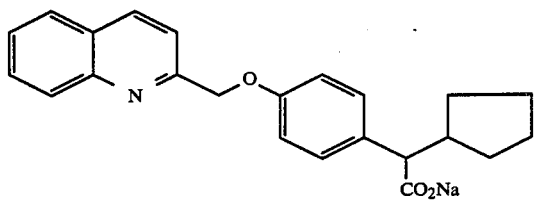

10 g (27.7 mmol) of 2-[4-(quinolin-2-yl-methoxy)-phenyl]-2-cyclopentylacetic acid are dissolved in 100 ml of water. After addition of 27.7 ml of 1 normal sodium hydroxide solution, the mixture is stirred at 25° C. for 1 hour and then concentrated and the residue is dried in vacuo at 100° C.

Yield: quantitative.
Melting point: >230° C.

EXAMPLE 23

Methyl 2-[4-(quinolin-2-yl-methoxy)phenyl]-3-cyclopentyl-propionate

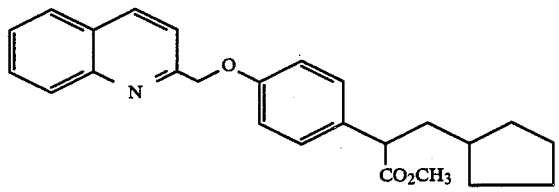

The preparation is carried out from 6.2 g (20 mmol) of methyl 4-(quinolin-2-yl-methoxy)phenylacetate and 3.3 g (20 mmol) of bromomethyl-cyclopentane analogously to the instructions of Example 2.

Yield: 5.1 g (65.5% of theory).
Melting point: 66°-68° C.

EXAMPLE 24

2-[4-(Quinolin-2-yl-methoxy)phenyl]-3-cyclopentyl-propionic acid

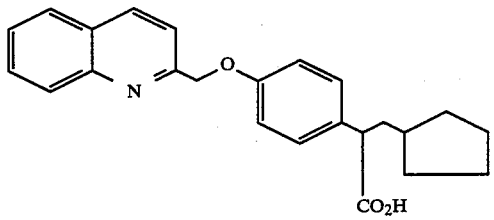

The preparation is carried out from 5 g (12.8 mmol) of methyl 2-[4-(quinolin-2-yl-methoxy)phenyl]-3-cyclopentyl-propionate analogously to the instructions of Example 7.

Yield: 2.5 g (52% of theory).
Melting point: 126°-128° C.

EXAMPLE 25

2-[4-(Quinolin-2-yl-methoxy)phenyl]-2-(cyclohex-2-enyl)acetic acid

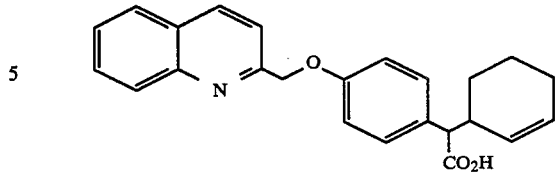

The preparation is carried out from 24.34 g (62.8 mmol) of methyl 2-[4-(quinolin-2-yl-methoxy)phenyl]-2-(cyclohex-2-enyl)-acetate analogously to the instructions of Example 7.

Yield: 18.3 g (78% of theory).
Melting point: 188°-192° C.

EXAMPLE 26

Carboxymethyl 2-[4-(quinolin-2-yl-methoxy)phenyl]-3-cyclopentylacetate

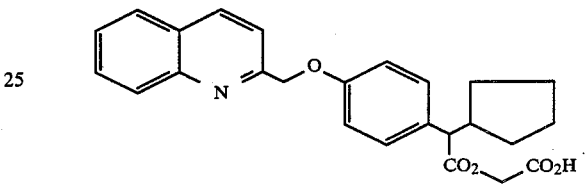

6.91 g (13.5 mmol) of benzyloxycarbonylmethyl 2-[4-(quinolin-2-yl-methoxy)-phenyl]-2-cyclopentyl-acetate are dissolved in 100 ml of ethyl acetate and 10 ml of triethylamine, 0.5 g of palladium catalyst (10% strength on charcoal) is added and hydrogenation is carried out under normal pressure at 25°. After uptake of the theoretical amount of hydrogen, the catalyst is filtered off. After concentration in vacuo, the residue is recrystallized from methanol.

Yield: 3.15 g (55.6% of theory.
Melting point: 168°-171° C.

EXAMPLE 27

Methyl 2-[4-(6-fluoroquinolin-2-yl-methoxy)phenyl]-2-cyclopentylacetate

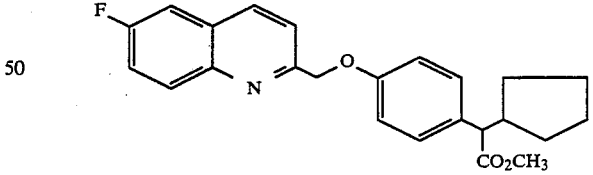

4.68 g (20.4 mmol) of methyl 2-[4-hydroxyphenyl)-2-cyclopentylacetate are dissolved in 50 ml of dimethylformamide. After addition of 2.82 g (20.4 mmol) of potassium carbonate, the mixture is stirred at 50° C. for 1 hour, 4 g (20.4 mmol) of 2-chloromethyl-6-fluoroquinoline are added and the mixture is stirred at 50° C. for a further 15 hours. After concentrating in vacuo, the residue is partitioned between water and ethyl acetate, the organic phase is dried over sodium sulphate and concentrated and the residue is recrystallized from methanol.

Yield: 7.36 g (91.6% of theory).
Melting point: 117°-119° C.

EXAMPLE 28

2-[4-(6-Fluoroquinolin-2-yl-methoxy)phenyl]-2-cyclopentylacetic acid

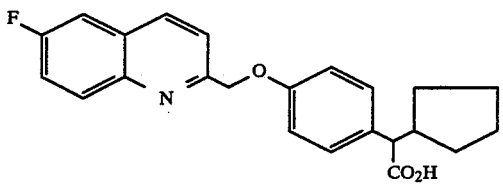

The preparation is carried out from 7 g (17.8 mmol) of methyl 2-[4-(fluoroquinolin-2-yl-methoxy)phenyl]-2-cyclopentyl-acetate analogously to the instructions of Example 7.

Yield: 4.51 g (67% of theory.
Melting point: 182°–184° C.

EXAMPLE 29

Methyl 2-[4-(quinolin-2-yl-methoxy)-phenyl]-2-norbornyl-acetate

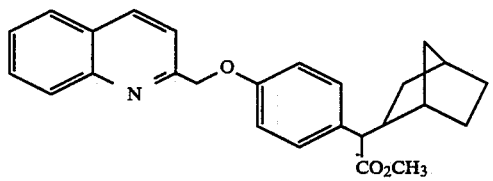

The preparation is carried out from 6.2 g (20 mmol) of methyl 2-[4-(quinolin-2-yl-methoxy)phenyl]-acetate and 3.5 g (20 mmol) of exo-2-norbornyl chloride analogously to instructions of Example 2. For purification: the product is Chromatographed on silica gel 60 (eluent: toluene/ethyl acetate 9:1)

Yield: 0.2 g (2.5% of theory).
Melting point: 123°–125° C.

EXAMPLE 30

2-[4-(Quinolin-2-yl-methoxy)phenyl]-2-norbornylacetic acid

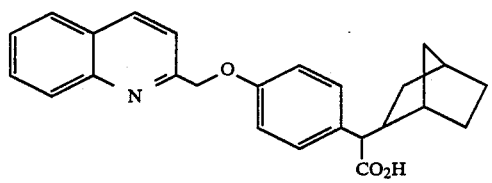

The preparation is carried out from 0.4 g (1 mmol) of methyl 2-[4-(quinolin-2-yl-methoxy)phenyl]-2-norbornylacetate analogously to the instructions of Example 7.

Yield: 0.36 g (93% of theory).
Melting point: 158°–160° C.

EXAMPLE 31

Methyl 4-benzyloxyphenylacetate

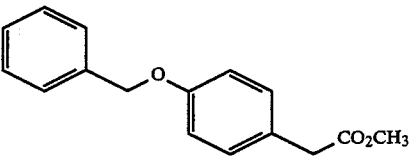

397 g of methyl 4-hydroxyphenylacetate and 330 g of potassium carbonate are stirred in 2 l of dimethylformamide at 25° C. for 1 hour. 302 g of benzyl chloride are then added and the mixture is heated at 50° C. for 15 hours. After concentrating in vacuo, the residue is partitioned between water and ethyl acetate and the organic phase is dried over sodium sulphate and concentrated. The product is recrystallized from methanol.

Yield: 511 g (83% of theory).
Melting point: 60° C.

EXAMPLE 32

Methyl 2-(4-benzyloxyphenyl)-2-cyclopentylacetate

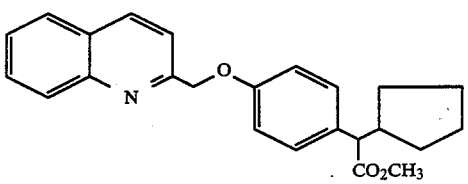

256.3 g (1 mol) of methyl 4-benzyloxyphenylacetate are dissolved in 1 l of dimethylformamide and the solution is added dropwise to a suspension of 24 g (1 mol) of sodium hydride in 100 ml of dimethylformamide at 0° C. under an inert gas (argon). When the evolution of $H_2$ has ended, the mixture is subsequently stirred at 0° C. for 2 hours. 149 g (1 mol) of cyclopentyl bromide, dissolved in 400 ml of dimethylformamide, are then added dropwise at the same temperature. When the addition has ended, the mixture is subsequently stirred at room temperature for 15 hours. The solvent is concentrated in vacuo and hot water (80° C.) is added to the residue. The mixture is cooled slowly, while stirring (KPG stirrer). The crystallized product is filtered off with suction, washed thoroughly with water, dried and recrystallized from methanol. Yield: 276 g (85% of theory).

Melting point: 77°–78° C. (methanol).

EXAMPLE 33

Methyl 2-cylcopentyl-2-(4-hydroxyphenyl)acetate

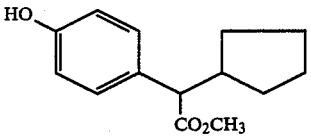

65 g (0.2 mol) of methyl 2-(4-benzyloxyphenyl)-2-cyclopentylacetate are dissolved in 100 ml of tetrahydrofuran, 200 ml of ethanol and 100 ml of triethylamine. After addition of 1.5 g of palladium catalyst (10% strength on charcoal), the mixture is hydrogenated under 3 bar of hydrogen for 2 hours. The catalyst is filtered off, the filtrate is concentrated and the residue is chromatographed on silica gel (eluent: methylene chloride). A viscous oil is obtained. Yield: 43.7 g (93% of theory)

EXAMPLES 34 A and 34 B

Diastereomers of 2-[4-(quinolin-2-yl-methoxy)-phenyl]-2-cyclopentylacetic acid [(L)-2-hydroxy-1-phenylethyl]amide

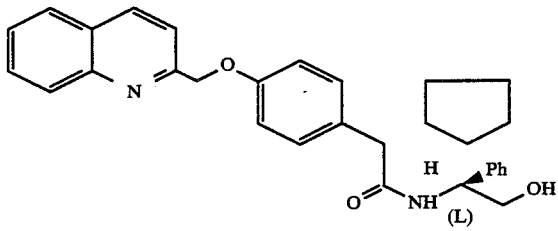

7.2 g (20 mmol) of 2-[4-(quinolin-2-yl-methoxy)phenyl]-2-cyclopentylacetic acid and 3.3 g (24 mmol) of (L)-phenylglycinol are dissolved in 100 ml of dimethylformamide. 6.6 g (24 mmol) of phosphoric acid diphenyl ester-azide in 25 ml of dimethylformamide are slowly added dropwise to the solution, which has been cooled to −10° C., 4.8 g (48 mmol) of triethylamine are then added and the mixture is stirred at −10° C. for 15 hours. The reaction mixture is poured onto ice and the crude product is filtered off, washed with water and dried. Recrystallization three times from ethanol gives diastereomer 34 A. Diastereomer 34 B is obtained by recrystallization of the combined mother liquors three times from methylene chloride.

Example 34 A: Yield: 1.93 g (20.1% of theory).
Melting point: 201°-203° C. (EtOH).
Example 34 B: Yield: 1.52 g (15.8% of theory).
Melting point: 158°-159° C. (CH$_2$Cl$_2$).

EXAMPLE 35

(+)-4-(2-Quinolin-2-yl-methoxy)phenyl]-2-cyclopentylacetic acid

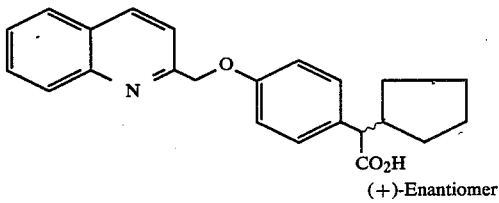

4.8 g (10 mmol) of diastereomer from Example 34 are heated under reflux in 50 ml of dioxane and 50 ml of 5 normal sulphuric acid for 24 hours. After cooling to 0° C., the pH is brought to 3 with 5 normal sodium hydroxide solution. The product is filtered off with suction and recrystallized from ethanol.

Yield: 2.38 g (65.8% of theory) $\alpha_D^{25}$= +40.9 (c=1, CHCl$_3$).
Melting point: 170°-172° C. (EtOH).

EXAMPLE 36

(−)-4-[2-Quinolin-2-yl-methoxy)-phenyl]-2-cyclopentylacetic acid

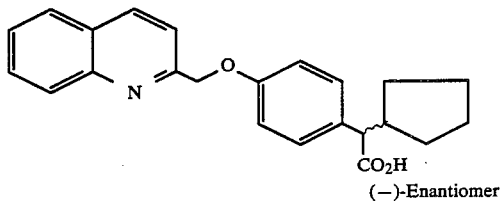

The preparation of compound 36 is carried out analogously to the instructions of Example 35 using 4.8 g (10 mmol) of diastereomer B from Example 34.

Yield: 2.28 g (63.2% of theory) $\alpha_D^{25}$= −40.7 (C=1, CHCl$_3$).
Melting point: 170°-172° C. (EtOH)

EXAMPLE 37 (use example)

The release of leucotriene B$_4$ (LTB$_4$) from polymorphonuclear rat leucocytes (PMN) following addition of substances and a Ca-ionophor was determined by means of reverse phase HPLC by the method of Borgeat, P. et al., Proc. Nat. Acad. Sci. (USA) 76, 2148-2152 (1979) as a measure of lipoxygenase inhibition.

The values achieved in this test with some compounds according to the invention are listed by way of example in Table 1:

TABLE 1

| Lipoxygenase inhibition | |
| --- | --- |
| Example No. | LO inhibition IC$_{50}$ (μM) |
| 7 | 0.14 |
| 8 | 0.01 |
| 9 | 0.04 |

We claim:
1. A substituted 4-(quinolin-2-61-methoxy)phenylacetic acid derivative of the formula

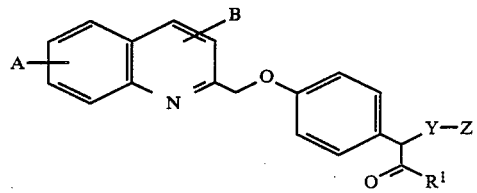

in which
R$^1$—represents a group of the formula

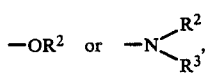

R$^2$ and R$^3$ are identical or different and—represent hydrogen, lower alkyl, phenyl, benzyl or a group of the formula

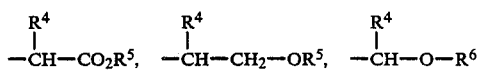

or 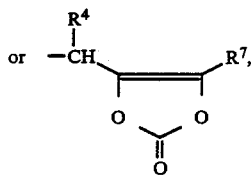

R[4]—represents hydrogen, lower alkyl, phenyl or benzyl, which can optionally be substituted by hydroxyl, carboxyl, lower alkoxycarbonyl, lower alkylthio, heteroaryl or carbamoyl, R[5]—represents hydrogen, lower alkyl, phenyl or benzyl, R[6]—represents a group of the formula —COR[5] or —CO$_2$R[5], R[7]—represents hydrogen, lower alkyl or phenyl, Y—represents a group of the formula

wherein

R[8]—represents hydrogen, lower alkyl or phenyl and n—denotes a number of 0 to 5, Z—represents norbornyl, or represents a group of the formula

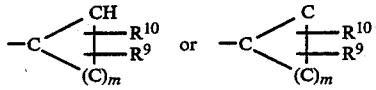

wherein

R[9] and R[10] are identical or different and denote hydrogen, lower alkyl or phenyl, or R[9] and R[10] can together form a saturated carbocyclic ring having up to 6 carbon atoms and m—denotes a number from 1 to 6, and A and B are identical or different and denote hydrogen, lower alkyl or halogen, or a pharmaceutically acceptable salt thereof.

2. A substituted 4-(quinolin-2-yl-methoxy)phenylacetic acid derivative or salt thereof according to claim 1, wherein

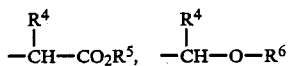

A and B are identical or different and denote hydrogen, methyl, ethyl, fluorine, chlorine or bromine.

3. A substituted 4-(quinolin-2-yl-methoxy)phenylacetic acid derivative or salt thereof according to claim 1, wherein R[1]—represents a group of the formula

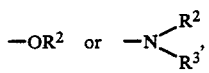

R[2] and R[3] are identical or different and—represent hydrogen, methyl, ethyl, propyl, isopropyl, butyl, tert.-butyl, phenyl or benzyl, or represent a group of the formula

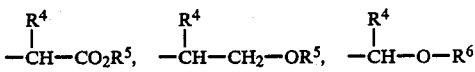

or 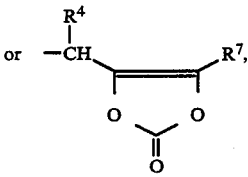

wherein

R[4]—represents hydrogen, methyl, ethyl, propyl, isopropyl, butyl, tert.-butyl, benzyl or phenyl, which can optionally be substituted by hydroxyl, methoxycarbonyl, ethoxycarbonyl, propoxycarbonyl, carboxyl, methylthio, ethylthio, propylthio, imidazolyl or carbamoyl, R[5]—represents hydrogen, methyl, ethyl, propyl, isopropyl, butyl, tert.-butyl, phenyl or benzyl, R[6]—represents a group of the formula —COR[5] or —CO$_2$R[5], and R[7]—represents hydrogen, methyl, ethyl, propyl, isopropyl, butyl, tert.-butyl or phenyl, Y—represents a group of the formula

wherein

R[8]—represents hydrogen, methyl, ethyl, propyl, isopropyl, butyl, tert.-butyl or phenyl, and n—denotes a number from 0 to 5, Z—represents norbornyl or represents a group of the formula

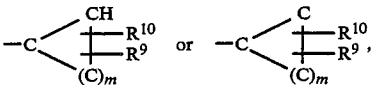

wherein

R[9] and R[10] are identical or different and denote hydrogen, methyl, ethyl, n-propyl, iso-propyl, butyl or tert.-butyl, or R[9] and R[10] can together form a saturated carbocyclic ring having up to 6 carbon atoms and m—denotes a number from 1 to 6, and A and B are identical or different and denote hydrogen, methyl, ethyl, fluorine or chlorine.

4. A substituted 4-(quinolin-2-yl-methoxy)phenylacetic acid derivative or salt thereof according to claim 1, wherein R[2] and R[3] are identical Dr different and—represent hydrogen or methyl, or—represent a group of the formula

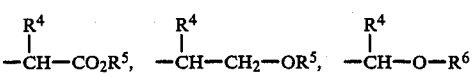

or 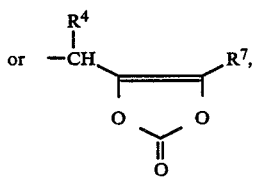

where
- $R^4$—represents hydrogen, methyl or phenyl,
- $R^5$—represents hydrogen, methyl, ethyl, tert.-butyl or benzyl,
- $R^6$—represents a group of the formula —$\overset{\text{O}}{\overset{\|}{C}}R^5$,
- $R^7$ represents methyl,
- $R^8$ represents hydrogen or methyl,
- n denotes the number 0 or 1,
- $R^9$ and $R^{10}$ are identical or different and denote hydrogen or methyl, or
- $R^9$ and $R^{10}$ together form a cyclohexyl ring, and
- m—denotes the number 1, 2, 3, 4 or 5, and
- A and B denote hydrogen or fluorine.

5. A compound according to claim 1, wherein such compound is 2-[4-(quinolin-2-yl-methoxy)phenyl]-2-cyclopentylacetic acid of the formula

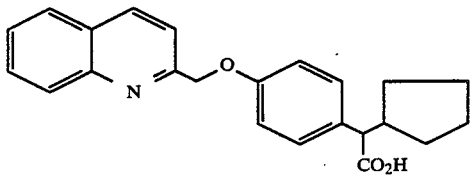

or a pharmaceutically acceptable salt thereof.

6. A compound according to claim 5, wherein such compound is the (+)-enantiomer.

7. A compound according to claim 5, wherein such compound is the (−)-enantiomer.

8. A compound according to claim 1, wherein such compound is 2-[4-(quinolin-2-yl-methoxy)phenyl]-2-cyclohexylacetic acid of the formula

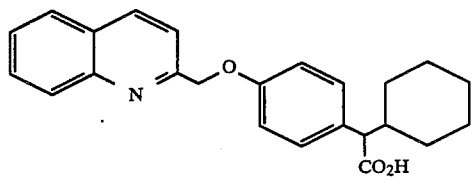

or a pharmaceutically acceptable salt thereof.

9. A compound according to claim 1, wherein such compound is 2-[4-(quinolin-2-yl-methoxy)phenyl]-2-cycloheptylacetic acid of the formula

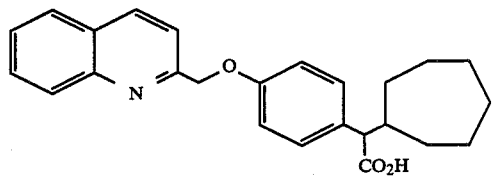

or a pharmaceutically acceptable salt thereof.

10. A leucotriene synthesis inhibiting composition comprising an amount effective therefor of a compound or salt according to claim 1 and a pharmacologically acceptable carrier.

11. A composition according to claim 10, in the form of a tablet, capsule or ampoule.

12. A method of inhibiting leucotrene synthesis in a patient in need thereof which comprises administering to such patient an amount effective therefor of a compound or salt according to claim 1.

13. The method according to claim 12, wherein such compound is
   2-[4-(quinolin-2-yl-methoxy)phenyl]-2-cyclopentylacetic acid,
   2-[4-(quinolin-2-yl-methoxy)phenyl]-2-cyclohexylacetic acid or
   2-[4-(quinolin-2-yl-methoxy)phenyl]-2-cycloheptylacetic acid.

14. The method according to claim 12, wherein such compound is the (+)-enantiomer of 2-[4-(quinolin-2-yl-methoxy)phenyl]-2-cyclopentylacetic acid.

15. The method according to claim 12, wherein such compound is the (−)-enantiomer of 2-[4-(quinolin-2-yl-methoxy)phenyl]-2-cyclopentylacetic acid.

* * * * *

UNITED STATES PATENT AND TRADEMARK OFFICE
CERTIFICATE OF CORRECTION

PATENT NO. : 4,970,215

DATED : November 13, 1990

INVENTOR(S) : Mohrs et al.

It is certified that error appears in the above-identified patent and that said Letters Patent is hereby corrected as shown below:

Col. 32, line 58    After formula insert -- wherein --

Col. 33, line 5    After formula insert -- wherein --

Col. 33, line 13    Delete " heteroaryl " and substitute -- imidazolyl --

Col. 33, line 53    Delete " $-\overset{R^4}{\underset{}{CH}}-CO_2R^5$, $-\overset{R^4}{\underset{}{CH}}-O-R^6$ Col. 33, line 65    After formula insert -- wherein --

Signed and Sealed this

Sixth Day of October, 1992

*Attest:*

DOUGLAS B. COMER

*Attesting Officer*    *Acting Commissioner of Patents and Trademarks*